United States Patent [19]

Crico

[11] 4,333,799
[45] Jun. 8, 1982

[54] PURIFICATION AND RECOVERY OF ETHYLENE DICHLORIDE

[75] Inventor: Aurelio M. Crico, Corpus Christi, Tex.

[73] Assignee: PPG Industries, Inc., Pittsburgh, Pa.

[21] Appl. No.: 216,038

[22] Filed: Dec. 15, 1980

Related U.S. Application Data

[63] Continuation of Ser. No. 61,711, Jul. 30, 1979, abandoned.

[51] Int. Cl.³ .............................................. B01D 3/40
[52] U.S. Cl. ..................................... 203/67; 570/238; 570/262
[58] Field of Search ................ 260/652 P; 203/67, 93, 203/94, 75, 78, 82, 84; 570/216, 238, 262

[56] References Cited

U.S. PATENT DOCUMENTS 3,061,652 10/1962 Clayton .......................... 260/652 P Primary Examiner—Frank Sever
Attorney, Agent, or Firm—George D. Morris; Edward J. Whitfield

[57] ABSTRACT

Ethylene dichloride is separated from unsaturated organic impurities such as trichloroethylene and benzene by extractive distillation in the presence of a high boiling chloroalkene solvent, such as perchloroethylene.

2 Claims, 3 Drawing Figures

PURIFICATION AND RECOVERY OF ETHYLENE DICHLORIDE

This is a continuation of application Ser. No. 61,711, filed July 30, 1979, now abandoned.

BACKGROUND OF THE INVENTION

Vinyl chloride is typically produced by pyrolysis of ethylene dichloride (1,2-dichloroethane), the latter being typically produced by an oxychlorination process wherein a gaseous mixture of ethylene, hydrogen chloride and oxygen is contacted with a Deacon-type catalyst at a moderately elevated temperature. Ethylene dichloride so produced typically contains unsaturated hydrocarbon and chlorohydrocarbon impurities, chief among which are benzene and trichloroethylene.

The presence of these unsaturated impurities tend to decrease the rate of the pyrolysis reaction of ethylene dichloride to vinyl chloride with the consequence that in order to maintain a given vinyl chloride production rate, the pyrolysis furnace must be operated at a higher temperature which results in a more rapid coking rate necessitating a higher than normal frequency of plant outages in order to decoke the furnace.

Unsaturated hydrocarbons or chlorohydrocarbon impurities are not easily or economically separated from ethylene dichloride by conventional distillation techniques. For example, trichloroethylene forms an azeotrope with ethylene dichloride and benzene (boiling point, 176.2° F.) has a volatility relative to ethylene dichloride (boiling point 183° F.) of only about 1.10. Consequently, purification distillation of ethylene dichloride containing unsaturated hydrocarbon and chlorohydrocarbon impurities results in considerable quantities of these impurities being carried over with the ethylene dichloride due to both azeotropic entrainment in the case of trichloroethylene and to low relative volatility vis-a-vis ethylene dichloride in the case of, for example, benzene.

STATEMENT OF THE INVENTION

In the distillation purification of ethylene dichloride containing unsaturated hydrocarbon and chlorohydrocarbon impurities, wherein ethylene dichloride is recovered as a light fraction, entrainment of the unsaturated impurities in the ethylene dichloride light fraction is reduced by conducting the distillation in the presence of a chloroalkene solvent having a normal boiling point of at least 390° K., at atmospheric pressure.

DESCRIPTION OF THE INVENTION

In accordance with this invention, it has been found that in the purification of ethylene dichloride by fractional distillation, entrainment of unsaturated hydrocarbon and chlorohydrocarbon impurities in the ethylene dichloride, recovered as a light fraction, are reduced by conducting the distillation in the presence of a chloroalkene solvent having a normal boiling point of at least 390° K.

Although the invention is particularly adapted to separating ethylene dichloride from trichloroethylene and benzene impurities using perchloroethylene as the extractive distillant, it is contemplated that the invention in its broadest sense is equally applicable to separating ethylene dichloride from other organic impurities.

Figure 1:
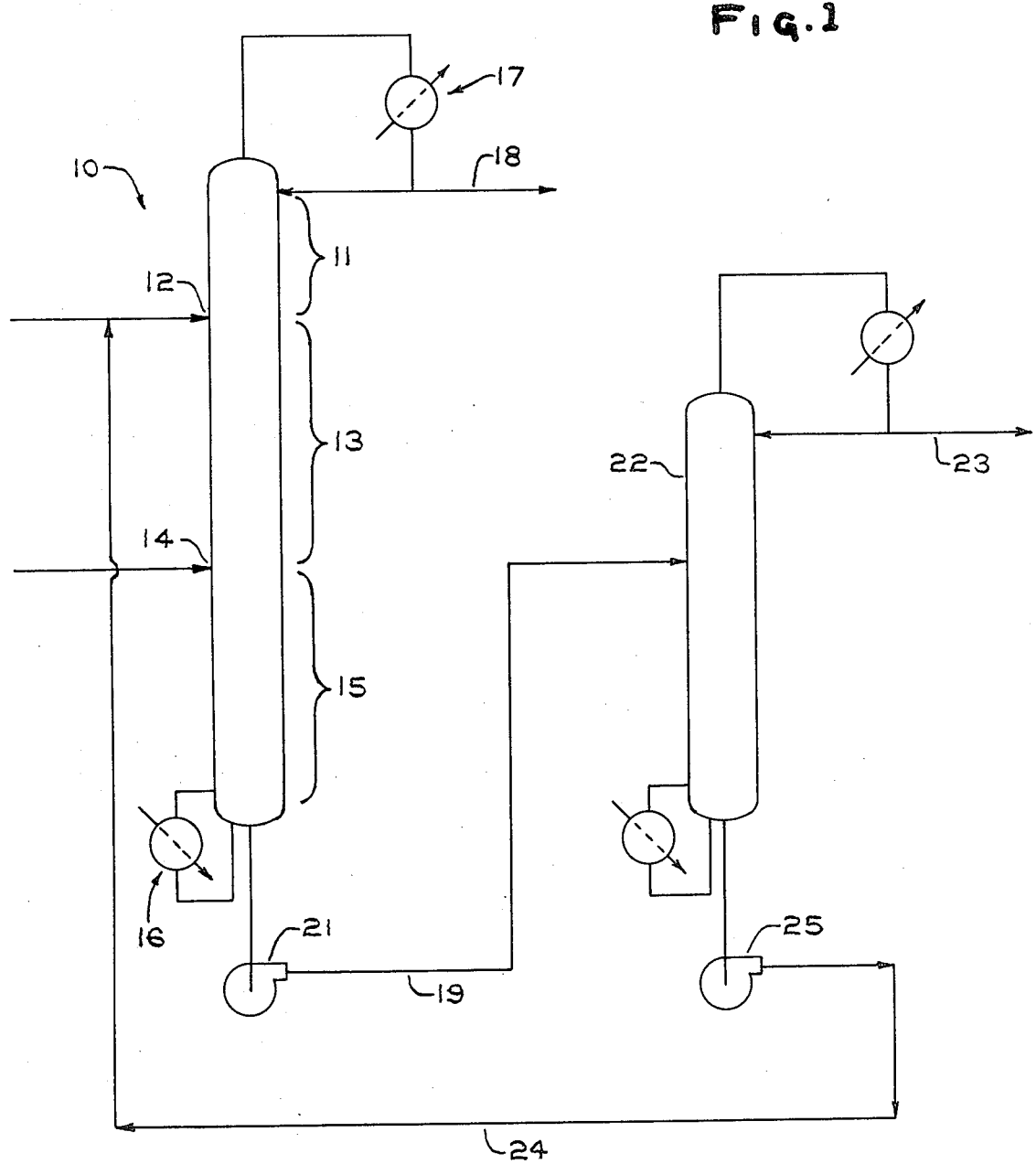
FIG. 1 is a simplified schematic drawing of a typical continuous rectifying/stripping apparatus and solvent recovery apparatus which may be used in the practice of the invention.

With reference to FIG. 1, 10 represents a conventional continuous distillation column having a top rectification section 11, located between the top of the column and the solvent feed point, 12, an extractive rectification section 13 located between the solvent feed point 12 and the primary feed point 14, and an extractive stripping section 15 located between the primary feed point 14 and the bottom of the column. The column is also provided with reboiler means 16 and reflux means 17. In operation, a liquid solvent is introduced at solvent feed point 12 and vaporous crude ethylene dichloride is introduced at primary feed point 14. The down flowing solvent contacts the vaporous feed in extractive rectification section 13 wherein light feed components, i.e., ethylene dichloride are separated from heavy feed components, including unsaturated organic impurities and thence to the extractive stripping section 15 wherein light feed components, i.e., ethylene dichloride, are stripped from the heavy feed components including unsaturated organic impurities. Sufficient solvent is used so as to provide and maintain at least about 30 and preferably at least about 50 mole percent solvent based on the solvent and crude ethylene dichloride fed to the column. For example, assuming n moles per hour of crude liquid ethylene dichloride is vaporized and fed to the column, at least 0.43 n moles per hour of solvent would need be fed.

Purified ethylene dichloride is removed as a light fraction via line 18 and the solvent containing extracted heavies including unsaturated impurities is removed through line 19 via pump means 21 and is introduced to distillation column 22 wherein the extracted heavies are removed from the solvent as a light fraction via line 23 and the recovered solvent is recycled to column 10 via line 24 and pump means 25. Make-up solvent may of course be added as required.

Figure 2:
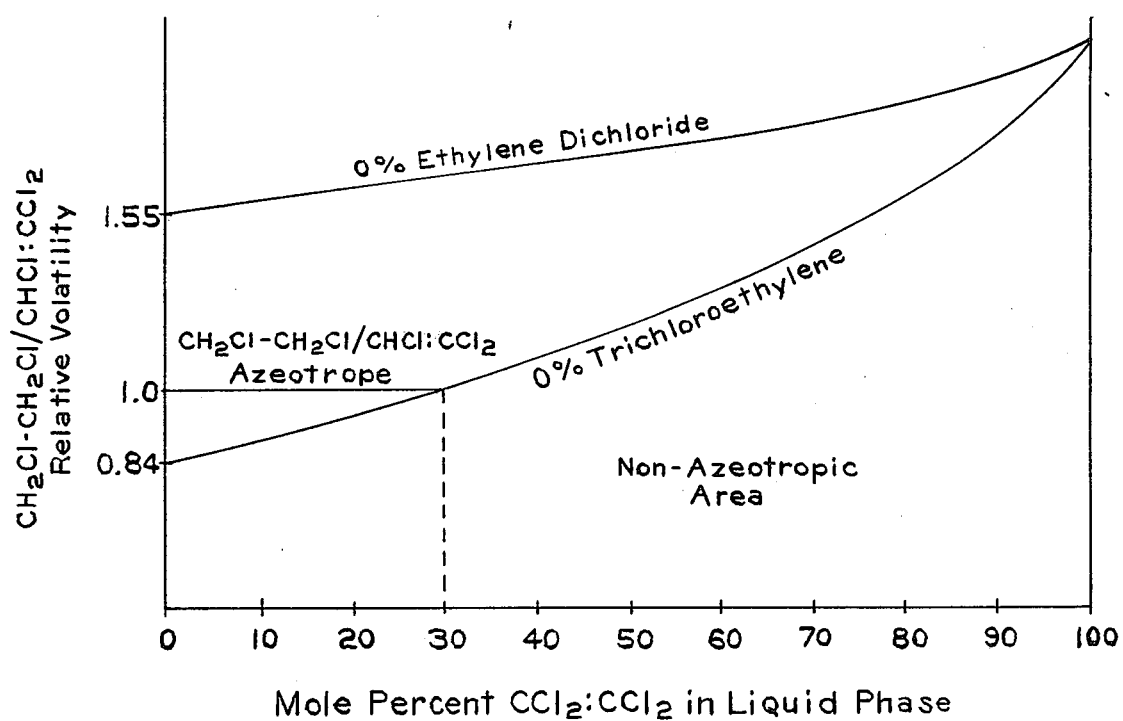
FIG. 2 is a diagram showing the effect of perchloroethylene concentration on the relative volatility of an ethylene dichloride-trichloroethylene mixture in the liquid phase at atmospheric pressure.
Figure 3:
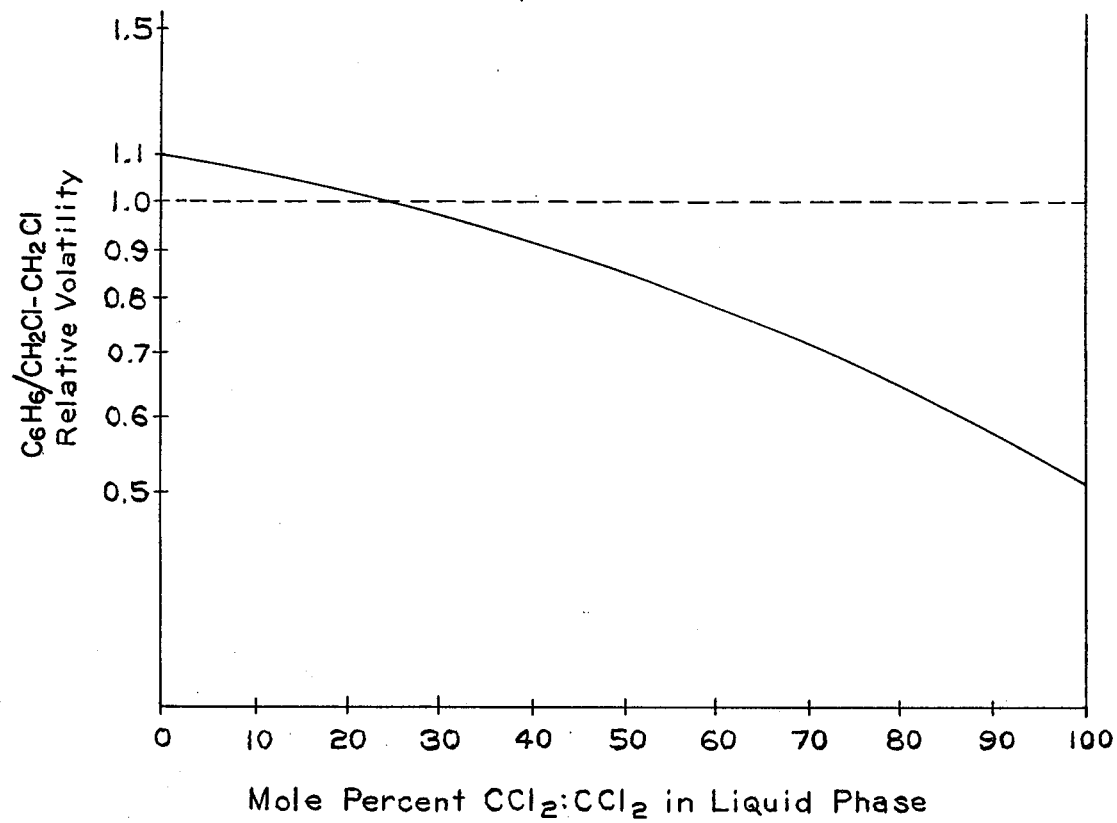
FIG. 3 is a diagram showing the effect of perchloroethylene concentration on the relative volatility of an ethylenedichloride-benzene mixture in the liquid phase at atmospheric pressure.

FIGS. 2 and 3 graphically illustrate the effect of perchloroethylene concentration on the relative volatility of an ethylene dichloride-trichloroethylene mixture and an ethylene dichloride-benzene mixture respectively.

With reference to FIG. 2, at zero perchloroethylene concentration, the relative volatility varies between 1.55 for 100 percent trichloroethylene and 0.84 for 100 percent ethylene dichloride with a relative volatility of 1.0 at the azeotrope concentration. It is seen from FIG. 2 that as perchloroethylene concentration increases, the ethylene dichloride-trichloroethylene ratio in the binary azeotrope also increases, and when perchloroethylene concentration exceeds about 30 mole percent, the relative volatility of the ethylene dichloride-trichloroethylene mixture becomes greater than 1. In other words, the azeotrope is broken permitting ready separation of ethylene dichloride from trichloroethylene.

With reference to FIG. 3, it is seen that although benzene and ethylene dichloride do not form an azeotrope, the volatility of benzene relative to ethylene dichloride is only about 1.10 and as perchloroethylene concentration increases, benzene to ethylene dichloride relative volatility decreases, the benzene in effect becoming heavier thus permitting ready separation of ethylene dichloride as a light fraction.

The invention thus provides a straightforward, expedient means of separating unsaturated organic impurities from ethylene dichloride which is further illustrated by the following examples.

EXAMPLE 1

The distillation unit used was a standard 1-inch diameter Oldershaw 58 plate column provided with an overhead condenser and a reboiler. A liquid mixture containing 5 mole percent benzene, 65 mole percent ethylene dichloride and 30 mole percent trichloroethylene was vaporized and fed to the column as a vapor at a temperature of 200° F. and a pressure of 18 psia. The vaporous mixture was fed at the 42nd plate counting from the top of the column. Perchloroethylene was heated to 250° F. and fed to the column at the 18th plate counting from the top in a 9:1 volume/volume ratio based on the liquid mixture. The column was operated at atmospheric pressure, at a reflux ratio (L/D) of 10, and a distillate temperature of about 160° F.

The material balance for the overhead distillate fraction and bottoms fraction is summarized as follows:

| | Overhead | | Bottoms | |
|---|---|---|---|---|
| Constituents | Concentration, Mole % | Recovery, % | Concentration, Mole % | Recovery, % |
| Ethylene Dichloride | 99.98 | 99.60 | 0.028 | 0.40 |
| Benzene | 0.001 | 0.14 | 0.534 | 99.86 |
| Trichloroethylene | 0.007 | 0.002 | 3.207 | 99.98 |
| Perchloroethylene | 0.002 | — | 96.231 | 100.00 |

EXAMPLE 2

A liquid mixture of ethylene dichloride containing 80 parts per million benzene, 4561 parts per million trichloroethylene and 8076 parts per million 1,1,2-trichloroethane and higher chlorinated ethanes was vaporized and fed to the column described in Example 1. The vaporous mixture was fed at the 42nd plate counting from the top of the column at a temperature of 200° F. and a pressure of 18 psia. Perchloroethylene was heated to 250° F. and fed to the column at the 18th plate counting from the top in 4:1 volume/volume ratio based on the liquid mixture. The column was operated at atmospheric pressure, at a reflux ratio (L/D) of 8 and a distillate temperature of about 160° F.

The material balance for the feed, overhead distillate fraction and bottoms fraction is summarized as follows:

| | | Overhead | | Bottoms | |
|---|---|---|---|---|---|
| Constituent | Feed, Mole % | Concentration, Mole % | Recovery, % | Concentration, Mole % | Recovery % |
| Ethylene Dichloride | 98.728 | 99.962 | 99.43 | 0.140 | 0.57 |
| Benzene | 0.008 | 0.001 | 12.04 | 0.002 | 87.96 |
| Trichloroethylene | 0.456 | 0.036 | 7.66 | 0.105 | 92.34 |
| Polychloroethanes | 0.805 | 0 | 0 | 0.210 | 100.00 |
| Perchloroethylene | 0.003 | 0.002 | 0.0005 | 99.544 | 99.99 |

Although the invention has been described with specific references and specific details of embodiments thereof, it is to be understood that it is not intended to be so limited since changes and alterations therein may be made by those skilled in the art which are within the full intended scope of this invention as defined by the appended claims.

I claim:
1. A process comprising:
   a. vaporizing n moles per hour of crude liquid ethylene dichloride containing trichloroethylene, benzene or a mixture thereof to form vaporous crude ethylene dichloride;
   b. feeding n moles per hour of said vaporous crude ethylene dichloride to a distillation column at a first feed point;
   c. feeding at least 0.43 n moles per hour of liquid perchloroethylene to said column at a second feed point located on said column above said first feed point;
   d. within said column, contacting vaporous crude ethylene dichloride with downflowing perchloroethylene, thereby stripping ethylene dichloride of trichloroethylene, benzene or a mixture thereof, and
   e. recovering, as a light fraction, ethylene dichloride having a reduced content of trichloroethylene, benzene or a mixture thereof.

2. The process of claim 1 wherein n moles per hour of perchloroethylene is fed to the column.

* * * * *